(12) United States Patent
Noh et al.

(10) Patent No.: US 10,481,058 B2
(45) Date of Patent: Nov. 19, 2019

(54) SAFETY TEST APPARATUS OF BATTERY CELL

(71) Applicant: LG Chem, Ltd., Seoul (KR)

(72) Inventors: Tae Gyun Noh, Daejeon (KR); Bum Young Jung, Daejeon (KR); Ki Woong Kim, Daejeon (KR); Hee Soo Na, Daejeon (KR); Oh Jun Kwon, Daejeon (KR)

(73) Assignee: LG Chem, Ltd., Seoul (KR)

( * ) Notice: Subject to any disclaimer, the term of this patent is extended or adjusted under 35 U.S.C. 154(b) by 143 days.

(21) Appl. No.: 15/724,720

(22) Filed: Oct. 4, 2017

(65) Prior Publication Data

US 2018/0095020 A1    Apr. 5, 2018

(30) Foreign Application Priority Data

Oct. 5, 2016  (KR) .................. 10-2016-0128584
Sep. 7, 2017  (KR) .................. 10-2017-0114415

(51) Int. Cl.
  *G01N 3/303* (2006.01)
  *H01M 10/48* (2006.01)
(52) U.S. Cl.
  CPC ............ *G01N 3/303* (2013.01); *H01M 10/48* (2013.01)
(58) Field of Classification Search
  CPC ............ G01N 3/30; G01N 3/303; G01N 3/34; G01N 3/48; G01M 7/08
  See application file for complete search history.

(56) References Cited

U.S. PATENT DOCUMENTS 4,085,609 A * 4/1978 Kelly .................. G01N 3/303
                                                                73/12.13

FOREIGN PATENT DOCUMENTS

| JP | H01173657 U | 12/1989 |
| KR | 10-0958649 B1 | 5/2010 |
| KR | 20110026864 A | 3/2011 |
| KR | 20140000398 A | 1/2014 |

* cited by examiner

*Primary Examiner* — Lisa M Caputo
*Assistant Examiner* — Alex T Devito
(74) *Attorney, Agent, or Firm* — Mintz Levin Cohn Ferris Glovsky and Popeo, P.C.; Kongsik Kim; Jhongwoo Jay Peck (57) ABSTRACT

The present invention relates to a safety test apparatus of a battery cell. The safety test apparatus of the battery cell comprises: a jig on which the battery cell is disposed on a top surface thereof; and an impact member comprising an impact rod supported on the top surface of the battery cell and a striking weight disposed above the jig to freely drop toward the jig and strike the impact rod so that an impact is applied to the battery cell, wherein the striking weight is provided in a pair and comprises left and right striking parts that respectively strike two striking points, which are spaced apart from each other, of the impact rod and a connection part connecting the left and right striking parts to each other.

14 Claims, 8 Drawing Sheets

SAFETY TEST APPARATUS OF BATTERY CELL

CROSS-REFERENCE TO RELATED APPLICATION

The present application claims the benefit of the priority of Korean Patent Application Nos. 10-2016-0128584, filed on Oct. 5, 2016, and 10-2017-0114415, filed on Sep. 7, 2017, which are hereby incorporated by reference in their entirety.

Technical Field

The present disclosure relates to a safety test apparatus of a battery cell, and more particularly, to a safety test apparatus of a battery cell, which measures a thermal image of the battery cell.

Related Art

In general, secondary batteries refer to chargeable and dischargeable, unlike primary batteries that are not chargeable. Recently, the secondary batteries have been widely used in the high-tech electronic fields such as mobile phones, notebook computers, and camcorders. Typically, a secondary battery is provided with one or more battery cells, and each of the battery cells comprises an electrode assembly and a case accommodating the electrode assembly.

The battery cells are subjected to a safety inspection hat include a thermal image test inspection. In particular, a safety test apparatus is used. The safety test apparatus includes a circular striking weight that strikes the battery cell to apply an impact and a thermal image measurement member measuring a thermal image of the battery cell to which the impact is applied. However, in the above-described safety test apparatus, a surface of the battery is substantially covered due to the shape of the striking weight. Accordingly, it is difficult to accurately measure the thermal image. A safety test apparatus which improves an impact member that strikes a battery cell to minimize a covered portion of the battery cell and thereby improve the accuracy of measurement of a thermal image is desired.

The above information disclosed in this section is merely for enhancement of understanding of the background of the disclosure and therefore it may contain information that does not form the prior art that is already known in this country to a person of ordinary skill in the art.

SUMMARY

The present disclosure provides a safety test apparatus which improves an impact member that strikes a battery cell to minimize a covered portion of the battery cell and improve the accuracy of a thermal image measurement. A safety test apparatus of a battery cell according to an embodiment of the present invention comprises a jig and an impact member. A battery cell is disposed on a top surface of the jig. The impact member comprises an impact rod supported on the top surface of the battery cell and a striking weight disposed above the jig to freely drop toward the jig and strike the impact rod so that an impact is applied to the battery cell. The striking weight is provided in a pair and comprises left and right striking parts that respectively strike two striking points, which are spaced apart from each other, of the impact rod and a connection part connecting the left and right striking parts to each other.

The two striking points of the impact rod may be disposed outside an edge of the top surface of the battery cell, and the left and right striking parts may strike the two striking points of the impact rod, respectively. The impact rod may have a cylindrical shape. The striking weight may have a '⊏' shape in which the left striking part, the connection part, and the right striking part are integrally connected to each other.

One or more holes for adjusting a weight of the striking weight may be formed in the striking weight. The holes may be symmetrically formed at left and right sides with respect to a vertical line (A) that equally divides the striking weight into the left and right sides.

The striking weight may further comprise a guide member guiding the striking weight to vertically drop toward the impact rod. The guide member may comprise a pair of guide rods and a guide part. The guide rods are vertically disposed on both ends of a top surface of the jig with respect to the battery cell, respectively. The guide part comprises a coupling piece disposed between the pair of guide rods and coupled to the striking weight and guide pieces respectively disposed on both ends of the coupling piece and coupled to the pair of guide rods so as to be slidably movable to allow the striking weight to vertically drop toward the impact rod.

The safety test apparatus may further comprise a driving member disposed above the jig to lift the striking weight upward or allow the striking weight to freely drop. A fixing part fixing the battery cell to prevent the battery cell from moving may be provided on the jig. The safety test apparatus may further comprise a thermal image measurement member measuring a thermal image of the battery cell to which the impact is applied by the impact member.

A support supporting the impact rod to prevent the impact rod from moving may be provided on the jig. The support may be provided in a pair so that the pair of supports are respectively disposed on one side and the other side of a top surface of the jig, on which both ends of the impact rod are disposed, to respectively support both side surfaces of the impact rod. The striking weight may be coupled to be slidably movable in a longitudinal direction of the coupling piece to adjust position errors of the striking weight and the impact rod.

BRIEF DESCRIPTION OF THE DRAWINGS

The above and other aspects, features and other advantages of the present disclosure will be more clearly understood from the following detailed description taken in conjunction with the accompanying drawings, in which.

EXEMPLARY EMBODIMENTS

Hereinafter, embodiments of the present disclosure will be described in detail with reference to the accompanying drawings in such a manner that the technical idea of the present disclosure may easily be carried out by a person with ordinary skill in the art to which the disclosure pertains. The present disclosure may, however, be embodied in different forms and should not be construed as limited to the embodiments set forth herein. In the drawings, anything unnecessary for describing the present disclosure will be omitted for clarity, and also like reference numerals in the drawings denote like elements.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. For example, in order to make the description of the present disclosure clear, unrelated parts are not shown and, the thicknesses of layers and regions are exaggerated for clarity. Further, when it is stated that a layer is "on" another layer or substrate, the layer may be directly on another layer or substrate or a third layer may be disposed therebetween.

It will be understood that, although the terms first, second, etc. may be used herein to describe various elements, these elements should not be limited by these terms. These terms are only used to distinguish one element from another. For example, a first element could be termed a second element, and similarly, a second element could be termed a first element.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

First Embodiment

Figure 1:
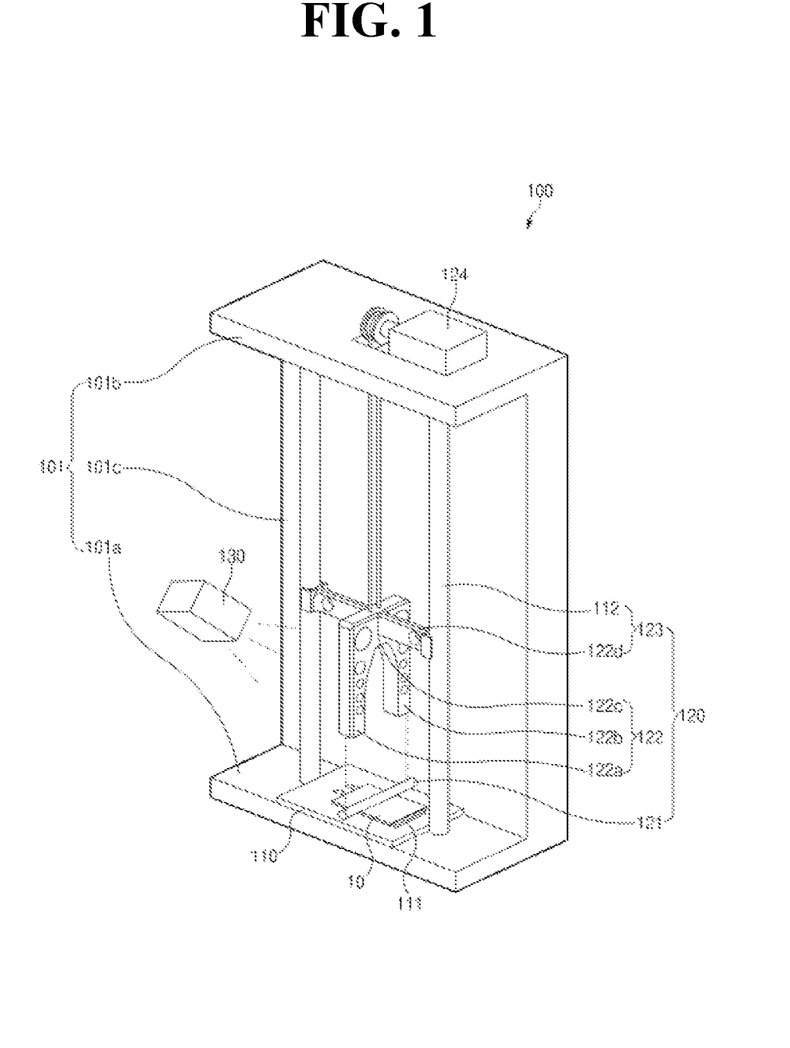
FIG. 1 is an exemplary perspective view illustrating a safety test apparatus of a battery cell according to a first exemplary embodiment of the present disclosure.
Figure 2:
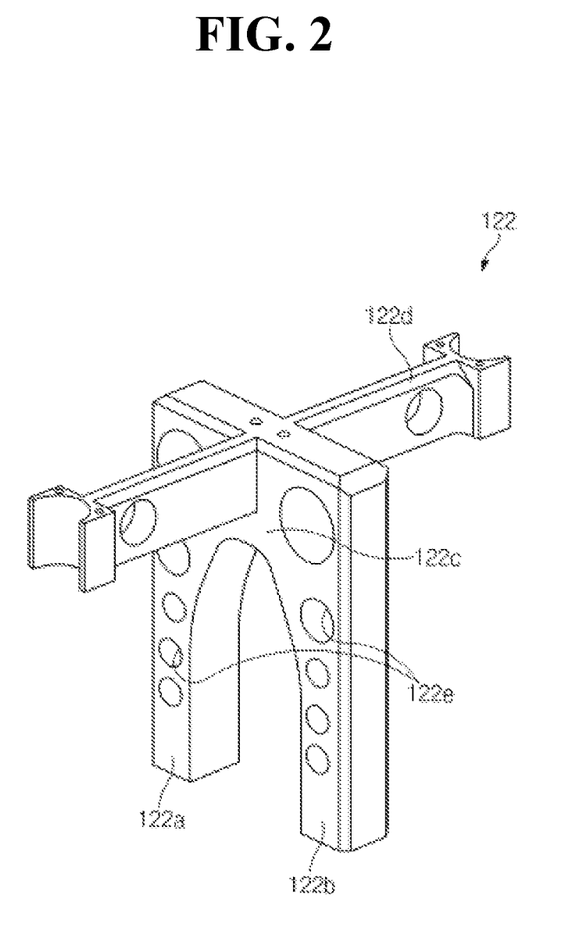
FIG. 2 is an exemplary perspective view of a striking weight according to the first exemplary embodiment of the present disclosure.
Figure 3:
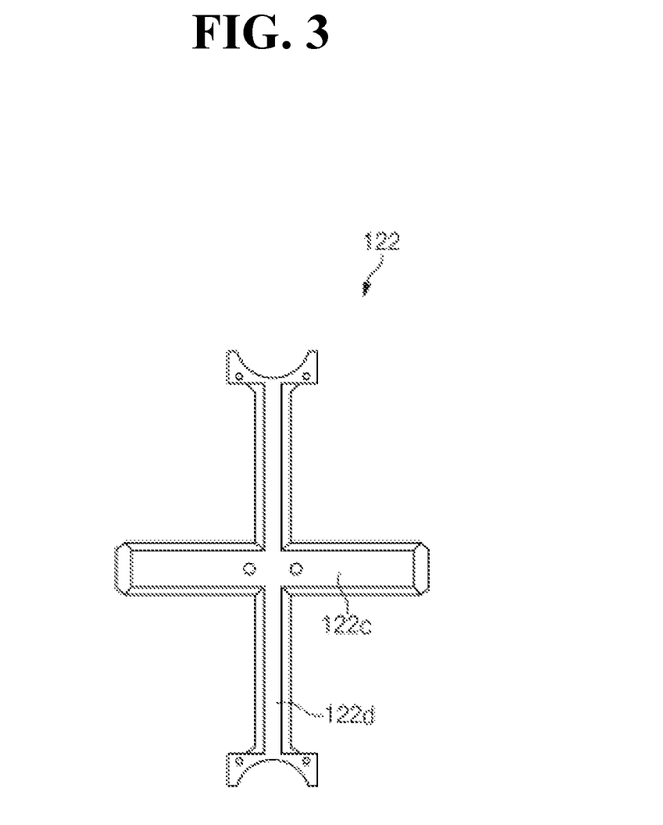
FIG. 3 is an exemplary plan view of the striking weight according to the first exemplary embodiment of the present disclosure.

In an exemplary embodiment, as illustrated in FIG. 1, a safety test apparatus 100 of a battery cell according to a first embodiment of the present invention comprises a jig 110 on which the battery cell 10 is disposed on a top surface thereof, an impact member 120 striking the battery cell 10 disposed on the jig 110 to apply an impact to the battery cell 10, and a thermal image measurement member 130 measuring a variation in thermal image of the battery cell 10 to which the impact is applied.

Referring to FIG. 1, the jig 110 is configured to fix the battery cell 10 and has a horizontal plane so that the battery cell 10 is disposed on the top surface thereof. Also, the jig 110 further comprises a fixing part 111 for fixing the battery cell 10 to prevent the battery cell 10 from moving. Thus, the fixing part 111 supports one or more surfaces of the battery cell 10 disposed on the jig 110 to prevent the battery cell 10 from moving in a front/rear or left/right direction. Here, the fixing part 111 may elastically fix the battery cell 10. Thus, the battery cell 10 may be more stably fixed from an external impact.

The jig 110 may be mounted on a main body 101 and thus stably fixed. The main body 101 comprises a lower plate 101a on which the jig 110 is mounted, an upper plate 101b disposed above the lower plate 101a, and a connection plate 101c connecting ends of the lower plate 101a and the upper plate 101b, which correspond to each other. Here, the jig 110 and the lower plate 101a may be integrated with each other.

The impact member 120 is configured to apply an impact to the battery cell 10 and comprises an impact rod 121 supported on the top surface of the battery cell 10 disposed on the jig 110 and a striking weight 122 which is disposed above the impact rod 121 and freely drops toward the impact rod 121 to strike the impact rod 121 and thereby to apply an impact to the battery cell 10. Here, the impact rod 121 may have two striking points spaced apart from each other. For example, the impact rod 121 may be formed in a long rod shape and have two striking points, which are spaced apart from each other, on both ends thereof. Thus, the striking weight 122 may strike both the ends of the impact rod 121 to minimize a portion of the battery cell 10, which is covered by the striking weight 122 and the impact rod 121.

Also, the impact rod 121 having the long rod shape may be disposed to be supported on the top surface of the battery cell 10 in a width direction. Thus, the portion of the battery cell 10, which is covered by the impact rod 121, may be minimized. Also, both the ends of the impact rod 121 having the long rod shape may be drawn out of the battery cell 10. Thus, the two striking points, which are spaced apart from each other, of the impact rod 121 may be disposed out of the battery cell 10 to prevent the battery cell 10 from being covered by the striking weight 122. That is, since the portion of the battery cell 10, which is covered by the striking weight 122, is removed, the variation in thermal image of the battery cell 10 may be more accurately measured.

The striking weight 122 is provided in a pair and comprises left and right striking parts 122a and 122b which strike the two striking points, which are spaced apart from each other, of the impact rod 121 and a connection part 122c connecting the left and right striking parts 122a and 122b to each other. For example, referring to FIG. 1, the striking weight 122 may have a '⊏' shape in which the left striking part 122a, the connection part 122c, and the right striking part 122b are integrally connected to each other. Thus, the left striking part 122a and the right striking part 122b may strike the two striking points of the impact rod 121 at the same time.

Figure 4:
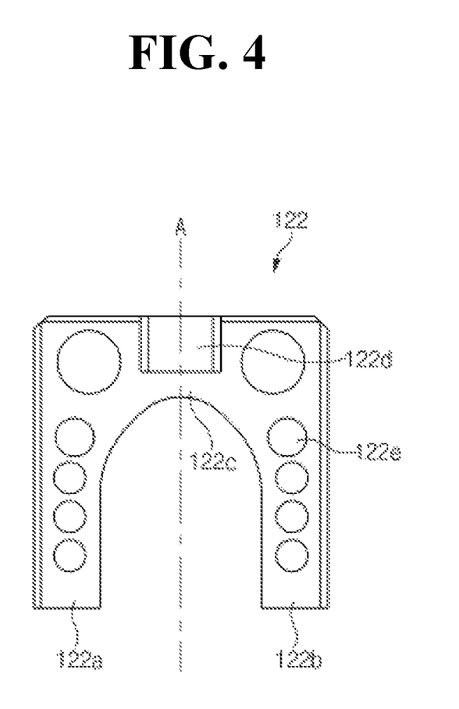
FIG. 4 is an exemplary front view of the striking weight according to the first exemplary embodiment of the present disclosure.
Figure 5:
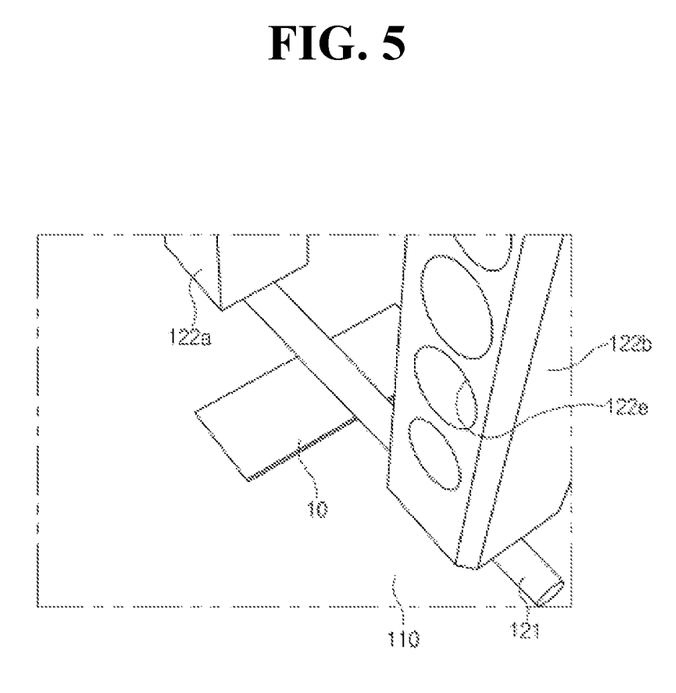
FIG. 5 is an exemplary perspective view illustrating a state in which the battery cell is struck in the safety test apparatus of the battery cell according to the first exemplary embodiment of the present disclosure.

One or more holes 122e for adjusting a weight may be formed in a surface of the striking weight 122. Thus, a weight of the striking weight 122 may be more precisely adjusted through the holes 122e. That is, a plurality of holes 122e may be formed in the surface of the striking weight 122. Here, each of the plurality of holes 122e may vary in size, i.e., may be adjusted to increase or decrease in size and thereby to adjust the weight of the striking weight 122. Here, as illustrated in FIG. 4, the holes 122e formed in the striking weight 122 may be formed at left and right side to be symmetrical to each other with respect to a vertical line A that equally divides the striking weight into the leaf and right sides. Thus, the left and right striking parts 122a and 122b of the striking part 122 may strike the two striking points of the impact rod 121 with the same force.

The impact member 120 having the above-described constituents may comprise the impact rod 121 and the striking weight 122 to minimize the covered portion of the battery cell 10 while maintaining the impact force applied to the battery cell 10 as it is. That is, since the battery cell 10 is covered by only the impact member 120 of the impact member 120, most of the surface of the battery cell 10 may be exposed to the outside, and thus, the variation in thermal image ma be more accurately measured.

The impact member 120 may further comprise a guide member 123 that guides the striking weight 122 so that the striking weight 122 vertically drops toward the impact rod 121. For example, the guide member 123 comprises a guide rod 112 vertically disposed on the top surface of the jig 110 or between the lower plate 101a and the upper plate 101b of the main body 101 on which the jig 110 is mounted and a guide part 122d disposed at one side of the striking weight 122 and coupled to the guide rod 112 so as to be vertically movable (i.e., to be vertically movable along the guide rod 112).

The guide rod 112 is provided in a pair. The pair of guide rods 112 are vertically disposed on both ends of the top surface of the jig 110 with respect to the battery cell 10, respectively. Here, the pair of guide rods 112 may be disposed in a longitudinal direction of the battery cell 10 so the guide rods are perpendicular to the impact rod 121. That is, the impact rod 121 is disposed on the top surface of the battery cell 10 in the width direction, and the pair of guide rods 112 are disposed in the longitudinal direction of the battery cell 10.

The guide part 112d comprises a coupling piece 122d-1 disposed between the pair of guide rods 112 and coupled to the striking weight 122 and a guide piece 122d-2 respectively disposed on both ends of the coupling piece 122d-1 and coupled to the pair of guide rods 112 so as to be slidably movable to guide the striking weight 122 so that the striking weight 122 vertically drops toward the impact rod 121. Here, the striking weight 122 and the coupling piece 122d-1 may be integrally coupled to each other to improve coupling force. Also, a guide groove 122d-3 that is closely surface-attached to a circumferential surface of the guide rod 112 may be formed in an outer surface of the guide piece 122d-2. Thus, the guide part 112d may stably slidably move along the guide rod 112 by the attachment force between the guide rod 112 and the guide groove 122d-3.

Auxiliary holes 122d-4 for reducing a weight may be formed in the coupling piece 122d-1. The auxiliary holes 122d-4 may be symmetrically formed at both sides with respect to a central point of the coupling piece 122d-1. Thus, in the guide member 123, when the striking weight 122 freely drops, the guide part 122d may be guided along the guide rod 112 to allow the striking weight 122 to vertically drop. As a result, the striking weight 122 may always strike the same striking portion of the impact rod 121 to obtain uniform striking force and impact force.

The impact member 120 further comprises a driving member 124 disposed above the jig 110 or on a top surface of the upper plate 101b of the main body 101 disposed above the jig 110 to lift the striking weight 122 upward or allow the striking weight 122 to freely drop. The driving member 124 may lift the striking weight 122 upward by using power, and then, when the power is removed, the striking weight 122 may freely drop by a weight thereof to strike the impact rod 121.

The thermal image measurement member 130 is configured to measure a thermal image of the battery cell 10 to which an impact is applied by the impact member 120. At least one or more thermal image measurement members 130 may be installed on a circumferential surface of the jig 110 to measure a variation in thermal image of the battery cell 10 to inspect safety of the battery cell 10 on the base of the measured values.

In the safety test apparatus 100 of the battery cell, which comprises the above-described constituents, according to the first embodiment of the present invention, the covered portion of the battery cell 10 after an impact is applied to the battery cell 10 may be minimized to more accurately measure the variation in thermal image of the battery cell 10. Hereinafter, a test method for the safety test apparatus 100 of the battery cell according to the first embodiment of the present invention will be described. First, the battery cell 10 is disposed on the top surface of the jig 110. Here, the battery cell 10 is disposed at a preset position of the jig 110, and them, the fixing part 111 moves to prevent the battery cell 10 from moving. Then, the impact rod 121 of the impact member 120 is supported on the top surface of the battery cell 10 in the width direction. Here, both the ends of the impact rod 121 are disposed to be drawn out of the battery cell 10 in the width direction. Also, the impact rod 121 may be fixed without moving through a separate elastic body or fixing body.

In this state, the striking weight 122 is lifted upward by using the power of the driving member 124, and then, the power of the driving member 124 is removed. As a result, the striking weight 122 vertically drops by the guide member 123 to strike the impact rod 121 and thereby to apply an impact. The impact force applied to the impact rod 121 is transmitted to the battery cell 10 to generate a variation in thermal image of the battery cell 10. Thus, the variation in thermal image of the battery cell 10 is measured by the thermal image measurement member 130 to inspect the safety of the battery cell 10. Here, since the battery cell 10 is covered by only the impact rod 121, most of the surface of the battery cell 10 may be exposed to the outside to more accurately measure the variation in thermal image of the battery cell 10.

Second Embodiment

Hereinafter, in descriptions of a safety test apparatus according to another embodiment of the present invention, constituents having the same function have been given with the same reference numeral in the drawings, and thus their duplicated descriptions will be omitted.

Figure 6:
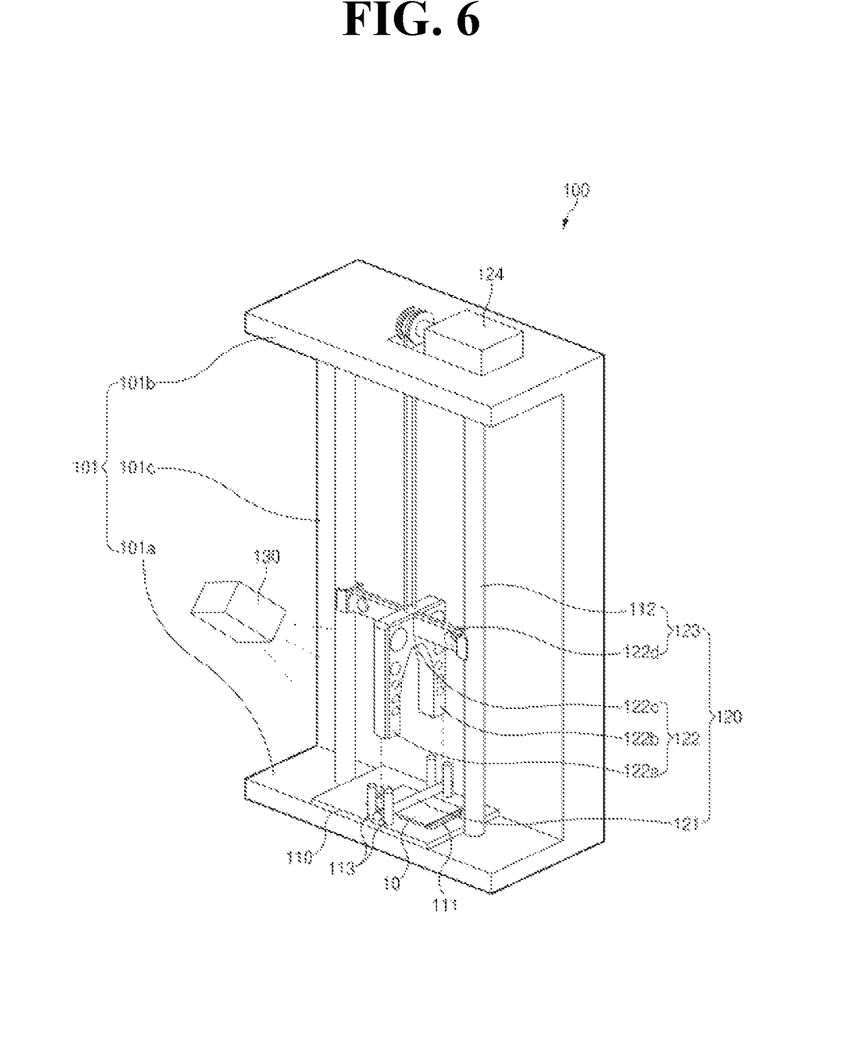
FIG. 6 is an exemplary perspective view illustrating a safety test apparatus of a battery cell according to a second exemplary embodiment of the present disclosure.
Figure 7:
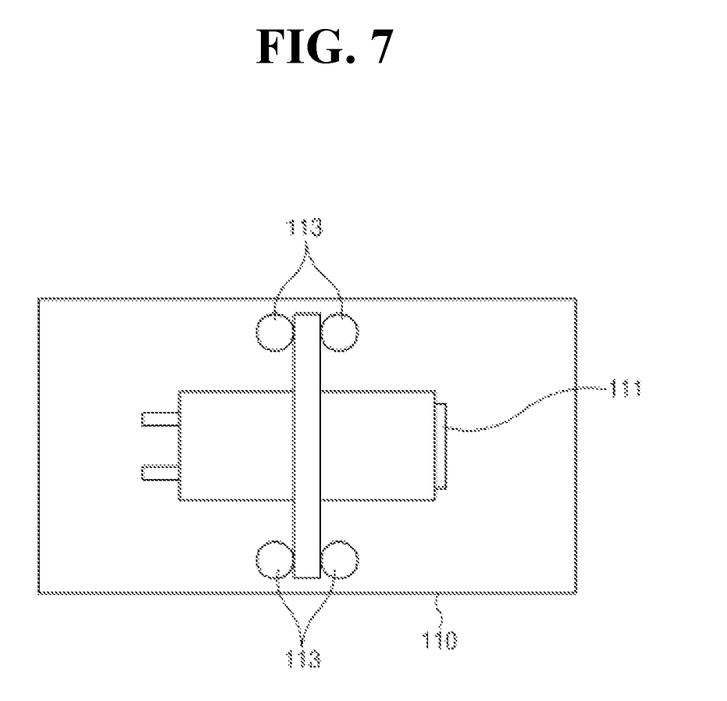
FIG. 7 is an exemplary plan view of a jig comprising a support in FIG. 6 according to an exemplary embodiment of the present disclosure.

As illustrated in FIGS. 6 and 7, a safety test apparatus of a battery cell according to a second embodiment of the present invention comprises a support 113 supporting an impact rod 121 disposed on the battery cell 10 to prevent the impact rod 121 from moving.

That is, the support 113 supporting the impact rod 121 to prevent the impact rod 121 from moving is disposed on a jig 110. The support 113 may be provided in a pair. Thus, the pair of supports 113 are disposed on one side and the other side of a top surface of the jig 110 to support both side surfaces of the impact rod 121, respectively. Here, the support 113 may be installed on the top surface of the jig 110 so as to be movable in a direction that is directed to the impact rod 121 or is opposite to the impact rod 121. Thus, the support 113 may move according to a size of the impact rod 121 to stably support the impact rod 121. Thus, the safety test apparatus of the battery cell according to the second embodiment of the present invention may comprise the support 113 to prevent the impact rod 121 from moving. Particularly, although a striking weight 122 strikes the impact rod 121, the impact rod 121 may be accurately struck because the impart rod 121 does not move.

Third Embodiment

Figure 8:
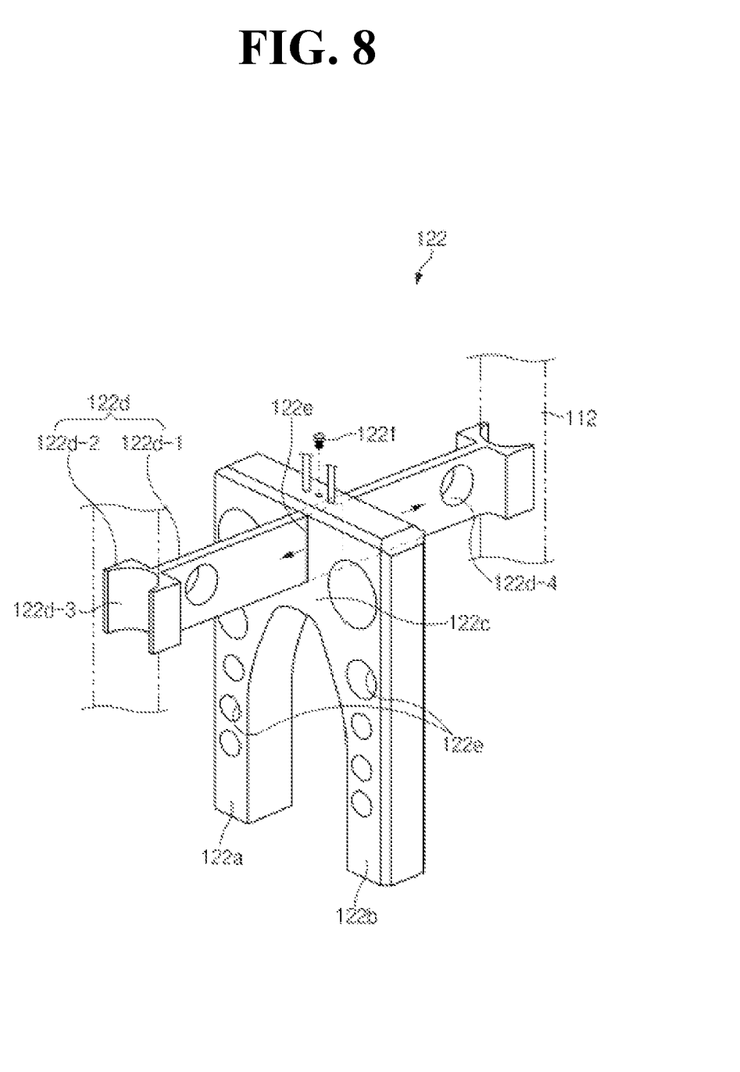
FIG. 8 is an exemplary perspective view illustrating a safety test apparatus of a battery cell according to a third exemplary embodiment of the present disclosure.

As illustrated in FIG. 8, a safety test apparatus of a battery cell according to a third embodiment of the present invention comprises a guide member 123 guiding an impact rod 121 so that a striking weight 122 vertically drops toward the impact rod 121. The guide member 123 comprises a pair of guide rods 112 vertically disposed on both ends of a top surface of a jig 110 with respect to the battery cell 10 and a guide part 122d comprising a coupling piece 122d-1 disposed between the pair of guide rods 112 and coupled to the striking weight 122 and guide pieces 122d-2 respectively disposed on each of both ends of the coupling piece 122d-1 and respectively coupled to the pair of guide rods 112 so as to be slidably movable and thereby to guide the striking weight 122 so that the striking weight 122 vertically drops toward the impact rods 121.

Here, the striking weight 122 may be slidably movably coupled in a longitudinal direction of the coupling piece 122d-1 to adjust position errors of the striking weight 122 and the impact rod 121. That is, the striking weight 122 may be adjusted in position so that the striking weight and the impact rod 121 are disposed in the same vertical line. For example, a through-hole 122e is formed in the striking weight 122. Also, the coupling piece 122d-1 has a bar shape with the same thickness and is slidably movably coupled to the through-hole 122e. Thus, the striking weight 122 may slidably move in a longitudinal direction of the coupling piece 122d-1 through the through-hole 122e. Thus, the striking weight 122 may be adjusted in position so that the striking weight 122 is disposed in the same vertical line as the impact rod 121 supported on the battery cell 10.

The guide member 123 may further comprise a fixing bolt 122f that fixes the striking weight 122 to the coupling piece 122d-1 or releases the fixing of the striking piece 122d-1 from the coupling piece 122d-1. As illustrated in FIG. 8, the fixing bolt 122f may press the coupling piece 122d-1 coupled to the through-hole 122e by passing through the top surface of the striking weight 122 or release the pressing with respect to the coupling piece 122d-1. Thus, the fixing bolt 122f may fix the striking weight 122 to the coupling piece 122d-1 to prevent the striking weight 122 from moving or release the fixing of the striking weight 122.

Thus, in the safety test apparatus of the battery cell according to the third embodiment of the present invention, the striking weight 122 may be coupled to be slidably movable in the longitudinal direction of the coupling piece 122d-1 to adjust the position errors of the striking weight 122 and the impact rod 121. Therefore, the striking weight 122 may accurately strike the impact rod 121 to improve accuracy of the safety test.

According to embodiments of the present invention, advantageous effects including the following may be achieved. First, the safety test apparatus of the battery cell may comprise the impact member provided with the impact rod and the striking weight to minimize the portion of the battery cell, which is covered by the impact member, and thereby to more accurately measure a variation in thermal image of the battery cell.

Second, in the safety test apparatus of the battery cell, the two striking points of the impact rod are formed to be drawn out of the battery cell, and the striking weight may strike the two striking point drawn out of the battery cell to more minimize the portion of the battery cell, which is covered by the impact member.

Third, in the safety test apparatus of the battery cell, the impact rod may be formed in the cylindrical shape to minimize the portion of the battery cell, which is covered by the impact rod.

Fourth, in the safety test apparatus of the battery cell, the striking weight may be formed in the '⊔' shape to minimize the portion of the battery cell, which is covered by the striking weight.

Fifth, the safety test apparatus of the battery cell may comprise the guide member to allow the striking weight to drop toward the impact rod, thereby always obtaining the same striking force.

Sixth, in the safety test apparatus of the battery cell, the guide member may comprise the guide rod and the guide part. Here, the striking weight may be coupled to be slidably movable in the longitudinal direction of the guide part to adjust the position errors of the striking weight and the impact rod. As a result, the impact rod may be accurately struck through the striking weight.

While the disclosure has been described with reference to the drawings according to the exemplary embodiments thereof, it will be understood by those skilled in the art that various changes and modifications may be made based on the descriptions given herein without departing from the scope of the disclosure.

The invention claimed is:

1. A safety test apparatus of a battery cell, the safety test apparatus comprising:
    a jig on which the battery cell is disposed on a top surface thereof; and
    an impact member comprising an impact rod supported on the top surface of the battery cell and a striking weight disposed above the jig to freely drop toward the jig and strike the impact rod so that an impact is applied to the battery cell,
    wherein the striking weight is provided in a pair and comprises left and right striking parts that respectively strike two striking points, which are spaced apart from each other, of the impact rod and a connection part connecting the left and right striking parts to each other.

2. The safety test apparatus of claim 1, wherein the two striking points of the impact rod are disposed outside an edge of the top surface of the battery cell, and
    the left and right striking parts strike the two striking points of the impact rod, respectively.

3. The safety test apparatus of claim 1, wherein the impact rod has a cylindrical shape.

4. The safety test apparatus of claim 1, wherein the striking weight has an inverted U-shape in which the left striking part, the connection part, and the right striking part are integrally connected to each other.

5. The safety test apparatus of claim 1, wherein one or more holes for adjusting a weight of the striking weight are formed in the striking weight.

6. The safety test apparatus of claim 5, wherein the holes are symmetrically formed at left and right sides with respect to a vertical line (A) that equally divides the striking weight into the left and right sides.

7. The safety test apparatus of claim 1, wherein the striking weight further comprises a guide member guiding the striking weight to vertically drop toward the impact rod.

8. The safety test apparatus of claim 7, wherein the guide member comprises:
- a pair of guide rods vertically disposed on both ends of a top surface of the jig with respect to the battery cell, respectively; and
- a guide part comprising a coupling piece disposed between the pair of guide rods and coupled to the striking weight and a guide piece respectively disposed on both ends of the coupling piece and coupled to the pair of guide rods so as to be slidably movable to allow the striking weight to vertically drop toward the impact rod.

9. The safety test apparatus of claim 1, further comprising a driving member disposed above the jig to lift the striking weight upward or allow the striking weight to freely drop.

10. The safety test apparatus of claim 1, wherein a fixing part fixing the battery cell to prevent the battery cell from moving is provided on the jig.

11. The safety test apparatus of claim 1, further comprising a thermal image measurement member measuring a thermal image of the battery cell to which the impact is applied by the impact member.

12. The safety test apparatus of claim 1, wherein a support supporting the impact rod to prevent the impact rod from moving is provided on the jig.

13. The safety test apparatus of claim 12, wherein the support is provided in a pair so that the pair of supports are respectively disposed on one side and the other side of a top surface of the jig, on which both ends of the impact rod are disposed, to respectively support both side surfaces of the impact rod.

14. The safety test apparatus of claim 8, wherein the striking weight is coupled to be slidably movable in a longitudinal direction of the coupling piece to adjust position errors of the striking weight and the impact rod.

* * * * *